United States Patent
Aho et al.

(10) Patent No.: US 10,786,148 B2
(45) Date of Patent: Sep. 29, 2020

(54) TUBE THORACOSTOMY USING AN OPTICAL TROCAR

(71) Applicant: Mayo Foundation for Medical Education and Research, Rochester, MN (US)

(72) Inventors: Johnathon M. Aho, Rochester, MN (US); Henry J. Schiller, Rochester, MN (US); Raaj K. Ruparel, Rochester, MN (US); Beth A. Ballinger, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 496 days.

(21) Appl. No.: 15/534,111

(22) PCT Filed: Dec. 9, 2015

(86) PCT No.: PCT/US2015/064793
§ 371 (c)(1),
(2) Date: Jun. 8, 2017

(87) PCT Pub. No.: WO2016/094559
PCT Pub. Date: Jun. 16, 2016

(65) Prior Publication Data
US 2017/0360290 A1 Dec. 21, 2017

Related U.S. Application Data

(60) Provisional application No. 62/196,710, filed on Jul. 24, 2015, provisional application No. 62/089,921, filed on Dec. 10, 2014.

(51) Int. Cl.
*A61B 1/313* (2006.01)
*A61B 1/00* (2006.01)

(52) U.S. Cl.
CPC ........ *A61B 1/3132* (2013.01); *A61B 1/00016* (2013.01); *A61B 1/00144* (2013.01); *A61B 1/00165* (2013.01)

(58) Field of Classification Search
CPC ........... A61B 1/00135; A61B 1/00016; A61B 1/00108; A61B 1/05; A61B 1/2676;
(Continued)

(56) References Cited

U.S. PATENT DOCUMENTS 4,633,304 A * 12/1986 Nagasaki ............... H04N 7/183
128/903
6,007,484 A 12/1999 Thompson
(Continued)

FOREIGN PATENT DOCUMENTS

WO    WO 2014/093401    6/2014

OTHER PUBLICATIONS

Aho et al., "A technique for visual confirmation of intrathoracic placement of tube thoracostomy using a fiberoptic laryngoscope in a cadaver," *Euro J Trauma Emerg Surg.*, 41(2):199-202, Apr. 2015.
(Continued)

*Primary Examiner* — Aaron B Fairchild
(74) *Attorney, Agent, or Firm* — Fish & Richardson P.C.

(57) ABSTRACT

Systems and methods that can improve the safety and efficacy of chest tube thoracostomy are described. For example, this document provides systems and methods that facilitate direct visual confirmation of the proper placement of a chest tube within the thoracic space.

6 Claims, 3 Drawing Sheets

(58) Field of Classification Search
CPC .................. A61B 1/313; A61B 1/3132; A61B 2017/0234; A61B 2017/0243
See application file for complete search history.

(56) References Cited

U.S. PATENT DOCUMENTS

| | | | |
|---|---|---|---|
| 2002/0193663 A1* | 12/2002 | Matsuura | A61B 1/00091 600/129 |
| 2005/0182297 A1 | 8/2005 | Gravenstein et al. | |
| 2007/0276183 A1 | 11/2007 | Melder | |
| 2010/0030057 A1 | 2/2010 | Gavriely et al. | |
| 2010/0179524 A1 | 7/2010 | Whayne et al. | |
| 2010/0199448 A1 | 8/2010 | Vazales et al. | |
| 2013/0253368 A1* | 9/2013 | Are | A61B 1/00016 600/560 |
| 2014/0228781 A1 | 8/2014 | Boyle | |
| 2015/0342699 A1* | 12/2015 | Cameron | A61B 1/04 600/424 |

OTHER PUBLICATIONS

Bailey., "Complications of tube thoracostomy in trauma," *J Accid Emerg Med.*, 17(2):111-114, 2000.

Chan et al., "Complication rates of tube thoracostomy," *Am J Emerg Med.*, 15(4):368-370, 1997.

Chen et al., "Video-Guided Tube Thoracostomy With Use of an Electrical Nonfiberoptic Endoscope," *Ann Thorac Surg.*, 96:1450-1455, 2013.

Dcneuville., "Morbidity of percutaneous tube thoracostomy in trauma patients," *Euro J Cardiothorac Surg.*, 22(5):673-678, 2002.

Etoch et al., "Tube thoracostomy. Factors related to complications," *Arch Surg.*, 130(5):521-525, May 1995, discussion 525-6.

Helling et al., "Complications following blunt and penetrating injuries in 216 victims of chest trauma requiring tube thoracostomy," *J Trauma.*, 29(10):1367-1370, Oct. 1989.

International Preliminary Report on Patentability in International Application No. PCT/US2015/64793, dated Jun. 22, 2017, pages.

International Search Report and Written Opinion in International Application No. PCT/US2015/64793, dated Mar. 11, 2016, 9 pages.

Mefire et al., "Indications and morbidity of tube thoracostomy performed for traumatic and non-traumatic free pleural effusions in a low-income setting," *Pan Afr Med J.*, 18:256, 2014.

Menger et al., "Complications following thoracic trauma managed with tube thoracostomy," *Injury.*, 43(1):46-50, Jan. 2012.

Sethuraman et al., "Complications of tube thoracostomy placement in the emergency department," *J Emerg Med.*, 40(1):14-20, 2011.

* cited by examiner

TUBE THORACOSTOMY USING AN OPTICAL TROCAR

CROSS REFERENCE TO RELATED APPLICATIONS

This application is a National Stage application under 35 U.S.C. § 371 of International Application No. PCT/US2015/064793, having an International Filing Date of Dec. 9, 2015, which claims the benefit of U.S. Provisional Application No. 62/089,921, filed Dec. 10, 2014, and U.S. Provisional Application No. 62/196,710, filed Jul. 24, 2015. The disclosures of the prior applications are considered part of and are incorporated by reference in the disclosure of this application.

BACKGROUND

1. Technical Field

This document relates to systems and methods that can improve the safety and efficacy of chest tube thoracostomy. For example, this document relates to systems and methods that facilitate direct visual confirmation of the proper placement of a chest tube within the thoracic space.

2. Background Information

Tube thoracostomy placement is the preferred treatment for various intrathoracic conditions that interfere with cardiopulmonary physiology. It is a commonly performed procedure in acute care, trauma, and pulmonary care situations. Despite being common, studies show complication rates for this procedure are high, ranging from 6% to 37% in several case series. In addition, many complications of improper chest tube placement are not immediately recognized. For example, a thoracic drainage tube often reaches within the thoracic cavity but is not positioned in such a way to offer ideal drainage, such as intrafissural (3%-11% occurrence) or intraparenchymal placement (6%-26% occurrence). These sub-optimally placed tube thoracostomies are only detected on frontal radiography 11% of the time. The clinical effects of these sub-optimal drains are not fully known, and the possibility of harm caused by sub-optimal drainage exists.

For a thoracostomy drain to function properly, it must be appropriately positioned within the thoracic space. Various techniques can be used to ensure the drain lies within the thorax but outside of vital intrathoracic structures. Such techniques include blunt dissection and digital exploration of the structures within the thorax and the thoracic wall. Direct visualization of the thoracostomy to confirm intrathoracic placement would be a useful adjunct to these techniques.

Thoracostomy (chest tubes) tubes are long, semi-stiff, clear plastic tubes that are inserted between the ribs into the chest so that they can drain collections of liquids or air from the thoracic space. If the lung has been compressed because of this collection, the lung can thereafter re-expand after the drainage of the liquids or air from the thoracic space.

SUMMARY

This document provides systems and methods that can improve the safety and efficacy of chest tube thoracostomy. For example, this document provides systems and methods that facilitate direct visual confirmation of the proper placement of a chest tube within the thoracic space.

In general, one aspect of this document features a chest tube thoracostomy system. The chest tube thoracostomy system includes a chest tube that defines a lumen therethrough; an optic probe comprising a shaft and a tip end, the optic probe configured for releasable engagement with the chest tube; and a viewing device configured for viewing images captured by the optic probe.

Such a chest tube thoracostomy system may optionally include one or more of the following features. The system may further comprise a light source, wherein light from the light source can be emitted from the tip end of the optic probe. The optic probe may comprise fiber optics. The optic probe may comprise a camera. The optic probe may comprise a lens disposed at the tip end. The tip end of the optic probe may be controllably deflectable. The shaft of the optic probe may be configured for releasable engagement with the lumen of the chest tube. In some embodiments, the optic probe is configured to wirelessly transmit images captured by the camera to the viewing device. Optionally, the viewing system may be battery operated such that the viewing system is cordless. The chest tube thoracostomy system may further comprise a sterile cover that is coupleable on the optic probe. The sterile cover may be configured as a single-use, disposable cover in some embodiments.

In another implementation, a method of installing a chest tube in a thoracic space of a patient includes: incising and dissecting a thorax of the patient to create an insertion pathway into the thoracic space; inserting a portion of the chest tube into the insertion pathway, wherein the chest tube is releasably engaged with an optic probe having a shaft and a tip end, and wherein the optic probe is coupled with a viewing device configured for viewing images captured at the tip end of the optic probe; advancing the chest tube and optic probe further into the thoracic space while viewing images, using the viewing device, of the thoracic region captured by the optic probe; and removing the optic probe from engagement with the chest tube while leaving the chest tube at least partially disposed within the thoracic region.

Such a method of installing a chest tube in a thoracic space of a patient may optionally include one or more of the following features. The method may further comprise attaching a proximal end portion of the chest tube to a vacuum source. The optic probe may be coupled to a light source, and light from the light source may be emitted from the tip end of the optic probe to illuminate the thoracic space. The optic probe may comprise fiber optics. The optic probe may comprise a camera. The optic probe may comprise a lens disposed at the tip end. The tip end of the optic probe may be controllably deflectable. The shaft of the optic probe may be releasably engaged with a lumen of the chest tube. The method may further comprise transmitting to a remote image storage system, via a computer network in communication with the viewing device, the images of the thoracic region captured by the optic probe.

Particular embodiments of the subject matter described in this document can be implemented to realize one or more of the following advantages. First, in some embodiments the systems and methods provided herein can be used to confirm whether a chest tube is properly placed within a patient's thoracic space. In some circumstances, such systems and methods can provide more a definitive confirmation of proper chest tube placement than current methods. For example, chest radiographs are sometimes currently used in attempt to confirm the proper placement of chest tubes. However, such radiographical images typically provide only two-dimensional visualization. Therefore, a chest radiograph may not provide a definitive confirmation of the three-dimensional location of the chest tube within the patient's thoracic space.

Second, in some embodiments the systems and methods provided herein can be used to verify proper chest tube placement with greater objectivity than some current techniques. For example, in another current technique used in attempt to confirm proper chest tube placement, an inspection of the passage of gas bubbles through a water-seal chest drainage unit is performed. However, such inspection is inherently subjective and prone to human error. In contrast, in some embodiments the devices and methods provided herein allow for objective detection and verification of the proper placement of chest tubes by facilitating direct visual confirmation of the proper placement of a chest tube within the thoracic space.

Third, in some embodiments the systems and methods provided herein can facilitate installation of chest tubes with a reduced risk of inducing trauma in comparison to traditional methods. For example, by facilitating direct visual confirmation of the proper placement of a chest tube within the thoracic space, the potential for causing injuries such as pulmonary lacerations or other trauma to the lung parenchyma can be reduced.

Fourth, in some embodiments the systems provided herein have wireless configurations for enhanced user convenience. For example, some embodiments of an optic probe for facilitating direct visual confirmation of the proper placement of a chest tube within the thoracic space can be configured to communicate wirelessly with a viewing system.

Other advantages will be discernable in view of the specification and figures described below.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides systems and methods that can improve the safety and efficacy of chest tube thoracostomy. For example, this document provides systems and methods that facilitate direct visual confirmation of the proper placement of a chest tube within the thoracic space.

In some embodiments, the devices and methods provided herein can be used to treat health conditions such as, but not limited to, pneumothorax. Pneumothorax (air in the pleural space) can be life-threatening. The immediate treatment for pneumothorax is tube thoracostomy, or the insertion of a chest tube. A long, flexible, hollow, narrow tube is inserted through the ribs into the pleural space, and the tube is attached to a suction device. This allows the air to be evacuated from the pleural space, and allows the lung to re-expand. Chest tubes are generally inserted using local anesthesia. The chest tube is left in place until the lung leak seals on its own, which usually occurs within two to five days.

Safe intrathoracic placement of chest tubes is a continual challenge. Current techniques for determining the intrathoracic location of the thoracostomy site include blunt dissection and digital exploration, with subsequent tube placement. Using current techniques, complication rates for this procedure approach 30%. Provided herein is a novel technique and system using optic probe technology for determining proper intrathoracic placement of tube thoracostomy under direct visualization.

Figure 1:
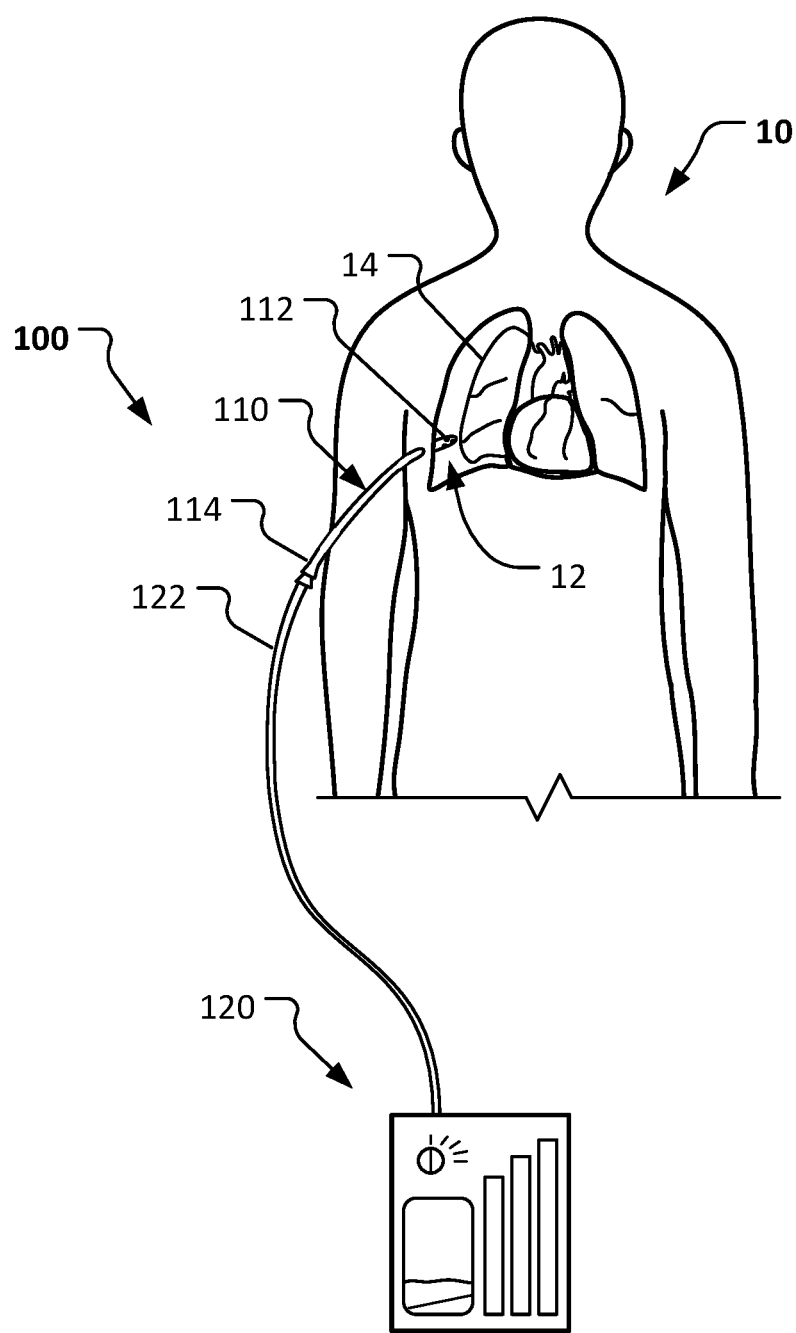
FIG. 1 is a schematic diagram of patient undergoing a chest tube thoracostomy in accordance with some embodiments provided herein.

Referring to FIG. 1, a patient 10 is undergoing a tube thoracostomy procedure using a tube thoracostomy system 100. Tube thoracostomy system 100 includes, in general, a chest tube 110 and a suction source such as a water-seal chest drainage unit (CDU) 120.

In this example, chest tube 110 is inserted into patient 10 and positioned so that a tip end portion 112 of chest tube 110 is located at a target thoracic space 12 near a partially collapsed lung 14 of patient 10. Tip end portion 112 includes one or more fenestrations so that the lumen of chest tube 110 is in fluid communication with thoracic space 12. A connection end portion 114 of chest tube 110 is connected to flexible tube 122 of CDU 120. CDU 120 thereby provides a source of suction that is conveyed through chest tube 110 to assist with evacuation of air and/or liquids from thoracic space 12.

As described further herein, during insertion into patient 10, the chest tube 110 may initially be engaged with a fiber optic trocar that can be used to facilitate direct visualization during insertion of chest tube 110. Such an arrangement can provide enhanced patient 10 safety and thoracostomy efficacy in some situations.

Figure 2:
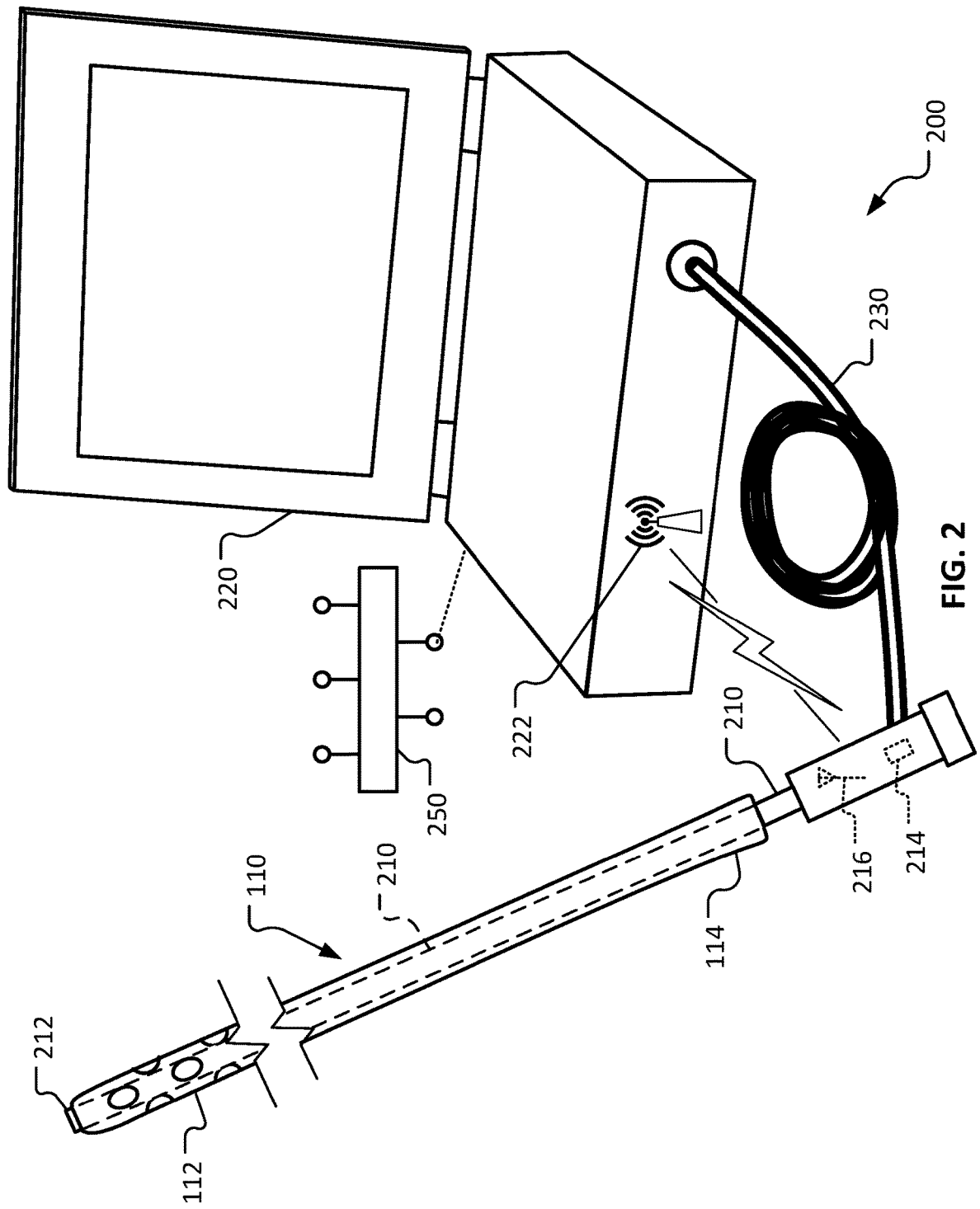
FIG. 2 is an illustration of an example system for preforming a thoracostomy using direct visualization in accordance with some embodiments provided herein.

Referring to FIG. 2, an example thoracostomy system 200 includes chest tube 110, a flexible optic probe 210, and a viewing system 220. Flexible optic probe 210 is slidably engaged within a central lumen of chest tube 110. In some embodiments, an optional cable 230 interconnects optic probe 210 with viewing system 220.

In some embodiments using cable 230, cable 230 includes a first fiber optic bundle that transmits light from a light source in viewing system 220 to a tip end 212 of optic probe 210. The light is emitted from tip end 212 to illuminate the field of view within the patient. Additionally, in some embodiments optic cable 230 includes a second fiber optic bundle that transmits the images received at tip end 212 of optic probe 210 to viewing system 220. The images are then displayed at viewing system 220 for a clinician's use.

One of skill in the art will recognize that design variations of the devices shown can be incorporated in thoracostomy system 200 without departing from the spirit of the inventive disclosure. For example, in some embodiments no viewing system 220 as shown is included. Rather, a clinician may view the images using an eyepiece on the end of optic probe 210, or using a hand-held LCD display device, or using other techniques.

In some embodiments, viewing system 220 is a personal computing device such as a laptop computer, smart phone, PDA, PC, or tablet computer, and the like. In some embodiments, viewing system 220 is a custom system designed for use in conjunction with optic probe 210. Viewing system 220 can be powered using AC electrical energy (e.g., from a wall socket) or DC electrical energy from a portable power source such as an on-board battery. Hence, in some embodiments no power cords are required for operating viewing system 220. Rather, viewing system 220 is a cordless configuration in some embodiments.

In some embodiments, rather than using fiber optics, a miniature camera (e.g., CCD-based) is located at tip end 212. In addition, a light source (e.g., a LED) can be located at tip end 212 in some embodiments. Hence, some such embodiments do not require the aforementioned fiber optic bundles that are located within optional cable 230. Instead, some embodiments using a miniature camera at tip end 212 of optic probe 210 (or elsewhere on optic probe 210) can facilitate wireless transmission of image information to viewing system 220, thereby eliminating the need for a hard-wired connection between optic probe 210 and viewing system 220. The wireless communications between optic probe 210 and viewing system 220 can use wireless communication modalities such as, but not limited to, Wi-Fi, BlueTooth®, WHDI Antenna Technology, RF, wirelessHD, and the like.

Wireless embodiments of optic probe 210 include an on-board power source 214 (such as one or more batteries), and electronic circuitry including a wireless signal transmission element 216 (such as one or more antennas). In some embodiments, two-way communication occurs between optic probe 210 and viewing system 220. In some embodiments, one-way communication occurs between optic probe 210 and viewing system 220 (i.e., from optic probe 210 to viewing system 220). Signals transmitted wirelessly between optic probe 210 and viewing system 220 can be communicated between wireless signal transmission element 216 and a wireless receiver or transceiver 222 coupled to viewing system 220.

In some embodiments, a lens is included at tip end 212 of optic probe 210. In some embodiments, the tip end 212 is steerable or deflectable. In any case, using thoracostomy system 200, the clinician can directly visualize the patient's internal anatomy in the path of tip end 212 during the placement of chest tube 110.

Prior to use, in some embodiments the clinician can slide the shaft of a sterile optic probe 210 into engagement with chest tube 110, such as within a lumen of chest tube 110. Alternatively, or additionally, a sterile cover may be placed on or over optic probe 210 prior to engaging optic probe 210 with chest tube 110. In some embodiments, the sterile cover may be a single-use, disposable cover. In some embodiments, the sterile cover may be a reusable, resterilizable cover. The optic probe 210 itself may be either a reusable, resterilizable item or a single-use, disposable item.

Proper operation of the viewing system 220 can be confirmed prior to insertion of chest tube 110 and optic probe 210 into the thoracic space. Incision, blunt dissection, and digital exploration of the patient's chest may have been performed in preparation for insertion of chest tube 110. Then, the clinician can insert the combination of chest tube 110 and optic probe 210 into the patient. During insertion and advancement of chest tube 110 and optic probe 210, the clinician operator can visualize the inner anatomy of the patient using viewing system 220. Such direct visualization can help facilitate a safe and effective thoracostomy procedure. That is, using the direct visualization provided by thoracostomy system 200 during installation of chest tube 110, the potential for traumatizing the patient's organs can be reduced, and proper positioning of chest tube 110 can be enhanced. After attaining the desired positioning of chest tube 110, the clinician can slidably remove optic probe 210 from engagement with chest tube 110 (while leaving chest tube 110 in situ).

In some embodiments, the images from optic probe 210 during insertion of chest tube 110 can be recorded and saved, if so desired. For example, in some embodiments the images can be saved by viewing system 220, either digitally (e.g., in RAM, hard disk memory devices, or optical devices), or in analog systems such as magnetic media.

In particular embodiments, viewing system 220 is in wired or wireless communication with a network 250. Network 250 may be various types of network systems including, but not limited to, a personal area network, a local area network, a wireless local area network, a wide area network (e.g., the internet), an enterprise private network (e.g., a hospital organization's network), and the like, and combinations thereof. In some such embodiments, images from optic probe 210 can be transferred to network 250 for archival storage, analysis, billing purposes, and the like. For example, images from optic probe 210 may be transferred to a hospital organization's networked picture archiving and communication system (PACS), as in a manner consistent with some other image guidance procedures.

Figure 3:
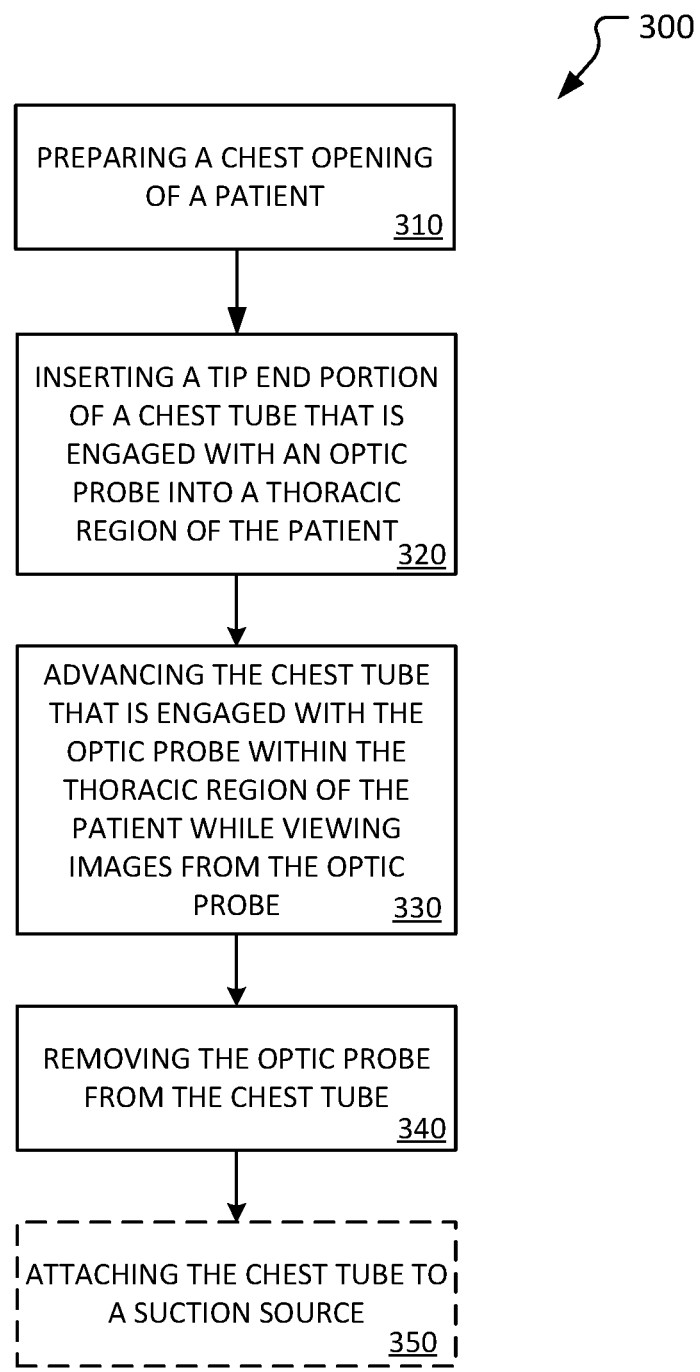
FIG. 3 is a flowchart of an example method for preforming a thoracostomy using direct visualization in accordance with some embodiments provided herein.

Referring to FIG. 3, a flowchart of an example thoracostomy method 300 is provided. Thoracostomy method 300 can be performed, for example, using thoracostomy system 200 as described above in reference to FIG. 2.

At step 310, a clinician can prepare a chest opening of a patient. Various techniques can be used. In some implementations, the clinician will make (in general) an incision, then perform blunt dissection and digital exploration of the structures within the thorax and the thoracic wall of the patient. The result of step 310 is a general pathway for insertion of a chest tube.

At step 320, the clinician inserts a tip end portion of a chest tube that is engaged with an optic probe into the thoracic region of the patient. In some embodiments, the chest tube that is engaged with the optic probe can be configured like thoracostomy system 200 as described above in reference to FIG. 2. The insertion location can be through the incision and general pathway created in step 310.

At step 330, the clinician advances the chest tube that is engaged with the optic probe within the thoracic region of the patient while viewing images from the optic probe. The images can be captured by the tip end of the optic probe. In some embodiments, a lens may be used at the tip end of the optic probe. The clinician can view the images in various ways. In some embodiments, the images are viewed on a display screen (e.g., an LCD screen). In some embodiments, the images care viewed using an eyepiece that is coupled to the optic probe. In some embodiments, other means of viewing the images can be used.

During the insertion and advancement of the chest tube that is engaged with optic probe, the clinician operator can visualize the inner anatomy of the patient using a viewing system. Such direct visualization can help facilitate a safe and effective thoracostomy procedure. That is, using direct visualization during installation of the chest tube, the potential for traumatizing the patient's organs can be reduced, and proper positioning of chest tube can be enhanced.

At step 340, the clinician removes the optic probe from engagement with the chest tube. The removal may be performed, for example, as a result of attaining a desired position of the chest tube within the patient thoracic region.

At step 350, the clinician can optionally connect the chest tube to a suction source. The suction source may be, for example, a type of water-seal chest drainage unit as described in reference to FIG. 1.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of installing a chest tube in a thoracic space of a patient, the method comprising:
   incising and dissecting a thorax of the patient to create an insertion pathway into the thoracic space;
   inserting a portion of the chest tube into the insertion pathway, wherein the chest tube is releasably engaged with an optic probe comprising:
      a shaft having a tip end;
      a light source operable to emit light from the tip end of the optic probe;
      a camera; and
      an on-board power source operable to power the light source and the camera,
      wherein the optic probe is configured for cordless operation, and wherein the optic probe is wirelessly coupled with a viewing device configured for displaying images captured at the tip end of the optic probe;
   advancing the chest tube and optic probe farther into the thoracic space while viewing images, using the viewing device, of a thoracic region captured by the optic probe; and
   removing the optic probe from engagement with the chest tube while leaving the chest tube at least partially disposed within the thoracic region.

2. The method of claim 1, further comprising, after removing the optic probe from engagement with the chest tube, attaching a proximal end portion of the chest tube to a vacuum source.

3. The method of claim 1, wherein the optic probe comprises a lens disposed at the tip end.

4. The method of claim 1, wherein the tip end of the optic probe is controllably deflectable.

5. The method of claim 1, wherein the shaft of the optic probe is releasably engaged with a lumen of the chest tube.

6. The method of claim 1, further comprising transmitting to a remote image storage system, via a computer network in communication with the viewing device, the images of the thoracic region captured by the optic probe.

* * * * *